US006451338B1

(12) United States Patent
Gregoriadis et al.

(10) Patent No.: US 6,451,338 B1
(45) Date of Patent: Sep. 17, 2002

(54) LIPOSOMES CONTAINING PARTICULATE MATERIALS

(75) Inventors: Gregory Gregoriadis, Northwood (GB); Sophia George Antimisiaris, Patras (GB); Ishan Gursel, Ankara (GB)

(73) Assignee: The Secretary of State for Defence in Her Britannic Majest's Government of the United Kingdom of Great Britain and Northern Ireland, Farnborough (GB)

(*) Notice: Subject to any disclaimer, the term of this patent is extended or adjusted under 35 U.S.C. 154(b) by 0 days.

(21) Appl. No.: 09/963,601

(22) Filed: Sep. 27, 2001

Related U.S. Application Data

(62) Division of application No. 08/624,556, filed on Sep. 20, 1996, now Pat. No. 6,322,809.

(30) Foreign Application Priority Data

Oct. 7, 1993 (GB) .............................. 9320668

(51) Int. Cl.[7] .............................. A61K 9/127
(52) U.S. Cl. ................. 424/450; 424/204.1; 424/234.1; 424/240.1; 424/246.1; 424/258.1; 424/265.1; 424/269.1; 264/4.1; 264/4.3; 264/4.6
(58) Field of Search .............................. 424/450, 204.1, 424/234.1, 240.1, 246.1, 258.1, 93.1, 265.1, 269.1; 264/4.1, 4.3, 4.6

(56) References Cited

U.S. PATENT DOCUMENTS

| 4,201,767 A | 5/1980 | Fullerton |
| 4,396,630 A | 8/1983 | Riedl et al. |
| 4,532,089 A | 7/1985 | MacDonald |
| 4,814,270 A | 3/1989 | Piran |
| 5,049,390 A | * | 9/1991 | Wojdain |
| 5,157,207 A | 10/1992 | Carlson |

FOREIGN PATENT DOCUMENTS

| EP | 0 171 710 | 2/1986 |
| EP | 0 172 007 | 2/1986 |
| GB | 2 066 203 A | 7/1981 |
| GB | 2 066 203 | 7/1981 |
| GB | 2 164 634 A | 3/1986 |
| WO | 86/01103 | 2/1986 |
| WO | 94/17786 | 8/1994 |

OTHER PUBLICATIONS

Shimizu et al "Encapsulation of chicken egg yolk immunoglobulin G (IgY) by Liposomes" Biosci–Biotechnical–Biochem, Sep. 1993; (abstract) New: "Liposome, A Pracical Approach," pp. 56–59, 94–97, Preparation of Liposomes.
Ohsawa et al "A Novel Method for Preparing Liposome with a High Capacity to Encapsulate Proteinous Drugs: Freeze–drying Method" Chem. Pharm. Bull. 32(6) 2442–2445 (1984).

* cited by examiner

Primary Examiner—Gollamudi S. Kishore
(74) Attorney, Agent, or Firm—Nixon & Vanderhye P.C.

(57) ABSTRACT

A method is provided for the formation of liposomes of 0.1 μm to 50 μm in diameter having unilamella or multilamella structure and containing water insoluble or undissolved particulate materials comprising (a) forming liposomes and removing substantially all of any organic solvent used in their preparation, (b) freeze drying the liposomes so formed and then (c) rehydrating them in intimate admixture with the particulate material. Preferred encapsulated materials are particulate materials, most preferably microorganisms, plant or animal cells or water insoluble structures having organic solvent labile biochemical or immunological activity, but any water insoluble particulate may be encapsulated using the method. For example catalysts or drugs that are sparingly soluble may also be so incorporated such that slow release into the a patients body may be provided while release of detergents included in the many liposome preparation protocols may be avoided.

11 Claims, 4 Drawing Sheets

LIPOSOMES CONTAINING PARTICULATE MATERIALS

Figure 1A:
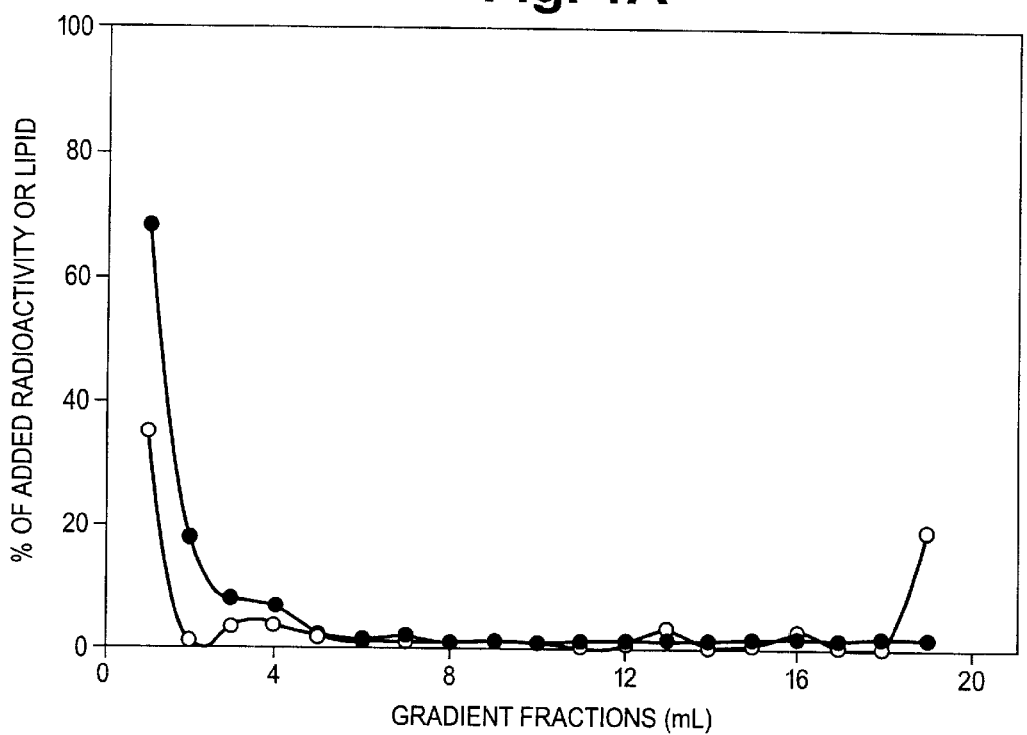
Figure 1B:
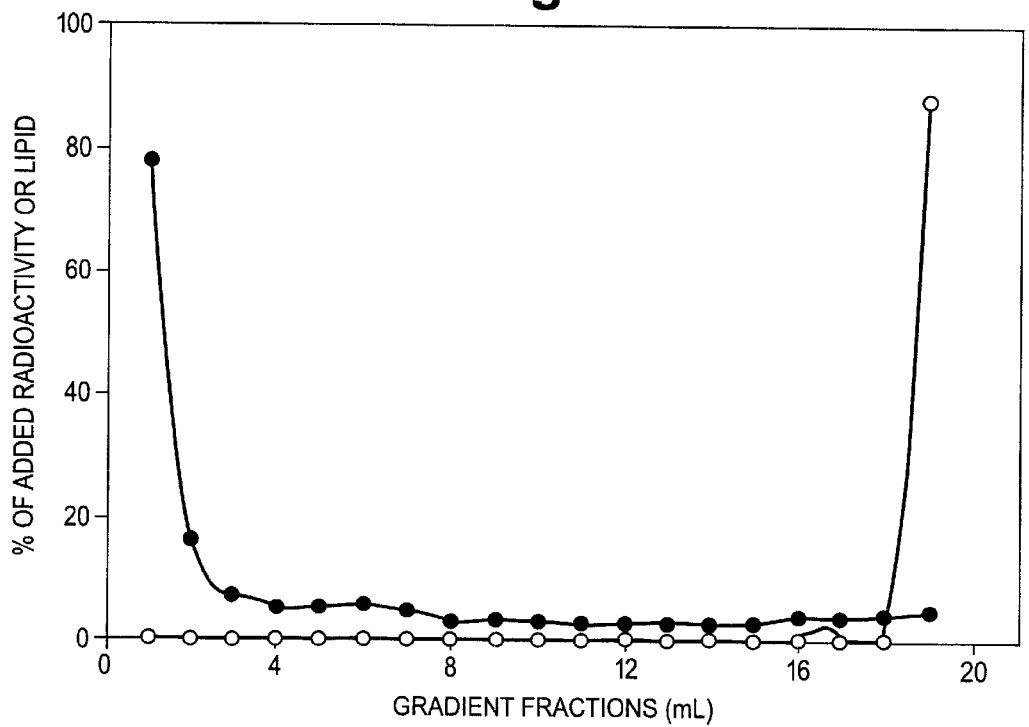

This application is a division of application Ser. No. 08/624,556 filed Sep. 20, 1996 now U.S. Pat. No. 6,322,809.

The present invention relates to liposome preparations capable of use in administration of organic solvent labile materials, such as whole live or attenuated cells, to human or animal bodies. Such preparations have utility in delivery of labile bioactive materials whereby a slow release is provided which may b e targeted to specific body areas. A method for the manufacture of such preparations is also provided.

The use of liposomes in the administration of vaccine agents is well known, and their adjuvant activity has been demonstrated by numerous studies into immunopotentiation of a large variety of bacterial, viral, protozoan, protein and peptide vaccines; see reviews by Gregoriandis G (1990) Immunol Today, 11, 89–97 and Alving C R (1991) J Immunol Meth, 140, p1–13.

These studies have all been carried out using liposomes produced by techniques which generate vesicles of submicron average diameter (see Gregoriadis G (ed) (1993) Liposome Technology, 2nd Edition, Volumes I-III CRC Press, Boca Raton, 1993) which are capable of accomodating peptides and proteins, but not capable of efficiently carrying larger vaccines. Such larger vaccines include a number of attenuated or killed viruses and bacteria such as measles, polio virus, *Bordetella pertussis*, Bacille Calmette-Guerin and *Salmonella typhi* (see Mimms C A et al (1993) Medical Microbiology, Chapter 36, Mosby).

Although most of these vaccines are highly immunogenic, there are circumstances where their administration in sufficiently large liposomes may be a preferred alternative. For instance, in the case of multiple vaccines consisting of a mixture of soluble and particulate (eg. microbial) antigens or vaccine formulations also containing cytokines, simultaneous presentation of all materials to immunocompetent cells via a common liposome carrier may be advantageous in terms of improving the immunogenicity to antigens.

Furthermore, liposomes incorporating antigenic material in their aqueous phase are known to prevent interaction of the antigen with its antibodies in pre-immunized animals and ensuing allergic reactions or antigen neutralisation (Gregoriadis and Allison (1974) FEBS Lett., 45, 71–74. It can thus be seen that liposomes could be beneficial if employed as carriers for administration of vaccines to infants for prophylaxis against agents for which maternal antibodies were present, eg, such as measles, or to individuals with hypersensitivity to vaccine contaminants.

It is known to incorporate particulate materials into large liposomes having average diameter up to 9.2 $\mu$m by methods wherein solvents such as chloroform are formed into spherules containing smaller water droplets (see Kim and Martin (1981) Biochimica et Biophysica Acta, 646, 1–9). Using this technique materials such as Collagen, DNA and bacteria (*Streptococcus salivarius*) were entrapped, but it was noted that labile globular proteins such as serum albumen and haemoglobin did not allow liposome formation, presumably due to surface denaturation, and that protein denaturation occurred. Such method is unsuitable for the encapsulation of labile materials due to the damaging and cytotoxic effects of the organic solvent, and certainly unsuitable for the encapsulation of whole (live) or attenuated bacteria, protozoa, viruses or multicellular animal or plant cells.

Methods for entrapping soluble materials in liposomes without use of organic solvents in the encapsulation step have been known for several years (see Kirby and Gregoriadis (1984) Liposome Technology, Vol I, Gregoriadis G (ed), CRC Press, Inc Boca Raton, Fla., pp 19–28; Deamer and Uster (1983) Liposomes, Ostro M J (ed) Marcel Dekker, Inc, NY. pp27–51; Deamer and Barchfield (1982) J Mol Evol 18, 203–206), and are based upon a method which dehydrates preformed liposomes then rehydrates them in the presence of the soluble materials. In these methods the soluble materials enter with water as the liposomes fuse together resulting in material being entrapped in multilamella liposomes. The liposomes used were 40 to 80 nm in diameter before freeze drying and the multilamellar product vesicle volume resulting was still smaller. Such volume and structure are unsuitable for encapsulating micrometer size and/or living materials, and entrapment levels for soluble drugs are not as high as for unilamella liposomes due to relatively low surface area for entry into the vesicles. The same technique has also been applied to small unilammela liposomes for the purpose of encapsulating aqueous solutions (see EP 0171710).

The aforesaid process is relatively mild and has been used to successfully encapsulate labile solutes such as factor VIII (see Kirby and Gregoriadis (1984) Biotechnology, 2, 979–984) and tetanus toxoid (Gregoriadis et al (1987) Vaccine, Vol 5, p145–151). It relies upon solute entering the liposomes as they form while rehydration water enters. Despite such work on solutes, there has still not been provided a method for the encapsulation of whole (live) or attenuated organisms, cells or other insoluble structures bearing labile entities, without damaging them; whether bacterial, protozoan, viral or otherwise.

Furthermore, no method has yet been provided for encapsulating water labile soluble materials in larger liposomes, whether unilamellar or multilamella, that would allow targeting at specific tissues with still higher quantities of material.

The present inventors have now surprisingly found that dehydration/rehydration is capable of successful encapsulation of insoluble particulates such as whole live or attenuated organisms, cells, or microscopic water insoluble structures having organic solvent labile activity, whereby organisms are not killed and activity is retained. The invention allows micrometer sized unilamella and multilamella liposomes to be produced, (ie. 0.1–50 $\mu$m diameter liposomes) which in contrast with the liposomes of the prior art, are capable of entrapping micrometer size and/or living material, and have inner vesicles of relatively high capacity, being similar in size to their outer diameter in the case of the unilamella giant liposomes.

It is particularly surprising that (i) when micrometer sized liposomes are dehydrated then rehydrated in this manner, unilamella liposome structure is retained which offers improved capacity for soluble material as well as the ability to retain particulates described above and (ii) where conditions are used such that multilamella liposomes are formed containing insoluble or undissolved material they are of micron size rather than the previously obtained 40 to 80 nm in diameter.

Thus in a first aspect of the invention there is provided a method for forming liposomes of greater than 0.1 $\mu$m diameter, preferably greater than 1 $\mu$m diameter, containing undissolved or insoluble particulate biologically, chemically or physically active material comprising (a) forming unilamellar liposomes (b) freeze drying the liposomes so formed and then (c) rehydrating them in intimate admixture with the undissolved or insoluble material to be contained therein.

Where unilamella liposomes are to be produced step (a) forms liposomes of greater than 0.1 $\mu$m in diameter and uses these in step (b). Where multilamella liposomes are to be produced the size of the liposomes need not be fixed in step (a), but determined by the undissolved or insoluble material with which they are preferably freeze dried with in step (b) prior to rehydration in step (c).

The freeze drying step is, in the case of both unilamella and multilamella liposomes, preferably carried out on a mixture of the liposomes and material to be entrapped and may be carried out by known methods for freeze drying liposomes. The rehydration step is preferably controlled such that the number of liposomes destroyed by osmotic pressures induced by solute concentrations generated by water entering the vesicles is minimised.

In a second aspect the present invention further provides liposomes produced by the method of the first aspect of the invention, and particularly provides liposomes characterised in that they are over 0.1 $\mu$m, preferably over 1 $\mu$m, in diameter and contain biologically, chemically or physically active materials that would have their activity damaged or destroyed by contact with organic solvents.

It is particularly preferred that substantially all of any organic solvent used in the step of liposome preparation (a) is removed prior to the rehydration step (c), most conveniently before the freeze drying step (b).

Preferred particulate materials are microorganisms, including bacteria, protozoa and viruses, plant or animal cells or water insoluble structures having organic solvent labile biochemical or immunological activity. It should be noted however that any water insoluble particulate may be encapsulated using the method. For example catalysts or drugs that are sparingly soluble may also be so incorporated such that slow release into the a patients body may be achieved. However, as organic solvents would not be expected to adversely affect these materials such method would be merely an option that might be used in place of the known methods; the main advantage of this preferred aspect of the present method being realised in its application to the organic solvent sensitive microorganisms, cells and materials, and in yielding increased capacity with multilamella liposomes.

Step (a) of forming the liposomes may use any of the known methods, including those involving use of solvents in their manufacture, as these remove such solvents to leave hollow bodies; the hollows forming the vesicles into which the solutions, microorganisms, cells or insoluble structures are to be situated after entrapment. Typically, for unilamella liposome production, the step (a) will comprise a method for the formation of so called 'giant liposomes' of suitable size for encapsulating the material added in step (c); such method being suitably eg. that of Kim and Martin described above. Most preferably these will be of 'micrometer' or 'micron' size', ie. herein defined as from 0.1 $\mu$m to 50 $\mu$m in diameter, more preferably 1 $\mu$m to 30 $\mu$m. For multilamella liposome production standard dehydration/rehydration vesicles (DRVs) may be formed.

For most satisfactory encapsulation rates the step of freeze drying step (b) is carried out with the material to be encapsulated already intimately mixed with the liposomes. In this manner relatively high encapsulation rates have been achieved whereas when the mixture of liposomes and material for encapsulation is not intimate enough, little or no incorporation is more likely. This is not the acse where solutions are being incorporated as in the prior art.

Step (c) may be carried out by any rehydration method that allows the liposomes to admit the material to be encapsulated. Conveniently this is found to include a procedure wherein water in any readily available form, eg.

distilled or tap water or a buffer solution, is added in a controlled manner to the freeze dried mixture of liposomes and material to be encapsulated. Preferably distilled water is first added in order to avoid still further osmotic stress to the liposome structure. Conveniently this is added in small quantity sufficient just to produce a suspension, followed after several minutes, preferably 20 to 40 minutes, eg. 30 minutes, by a similar amount of a buffer which is suitable for allowing the material to be encapsulated to retain its desired activity; one such suitable buffer being phosphate buffered saline (PBS) pH7.4. Again, the buffer is preferred at this stage in order to balance the high osomotic pressure of the solution forming in the vesicles of the liposomes as the materials present before the drying step are slowly rehydrated.

The suspension so obtained is preferably mixed with a larger volume of buffer, eg. PBS, after a further period, again preferably 20 to 40 minutes, preferably for about 30 minutes. The liposomes are typically freeze-dried from a suspension of liposomes, and the total volume of water and saline added in rehydration is conveniently sufficient to provide from 1 to 10 times that of the volume of the suspension, although no particular limits are placed here.

The rehydration step may be carried out at any temperature compatible with viability or retention of the desired activity of the material that is to be encapsulated. Thus typically any temperature from 0° C. to 60° C. might be selected where high melting point lipids are used in the liposomes and the material to be encapsulated is resistant to this temperature. Where living materials or proteins are used then 0° C. to 40° C. would be more usual, preferably 10° C. to 30° C. It will be realised however that certain organisms and proteins will be capable of treatment at much higher temperatures.

In order to maximise survival of the labile activity and the integrity of the liposomes in storage it may be advantageous to incorporate a cryoprotectant to counter the affects of freezing and water loss. This is preferably added after rehydration step (c) has been effected. Typical of such protectants are sugars and their derivatives, particularly sugars such as trehalose (see Crowe and Crowe in Liposome Technology (1993) V Vol I, pp229–249, CRC Press Inc, Boca Raton), with techniques for using this being well known to those skilled in the art.

The composition of the preformed liposomes provided in step (a) is also not particularly limited, but must allow for stable formation of liposomes having sufficient capacity to hold the material to be encapsulated. Typical lipid compositions used for formation of so called 'giant liposomes' and DRVs comprise phosphatidylcholine (PC) or distearoylphosphatidyl choline (DSPC), and these are optionally supplemented with components such as cholesterol, phosphatidyl glycerol (PG) and/or triolein (TO). Other components known in the art or developments thereof which provide liposome stability or induce vesicle formation may also be used.

Formation of giant liposomes from such mixtures is conveniently achieved by mixing a chloroform solution of these components with a sucrose solution to form and emulsion, then mixing that with a similar ether water emulsion to provide a water-in -oil-in-water emulsion, from which are removed the organic solvents to generate liposomes. Formation of DRVs may conveniently be achieved by dissolving equimolar PC, or DSPC, and cholesterol in chloroform and rotary evaporating the mixture to leave a thin film of lipid on a flask wall. This film is then disrupted at 4° C. (for PC) or 60° C. (for DSPC) with 2 ml distilled water followed by probe sonication for 2 minutes to yield small unilamella vesicles (SUVs). This suspension is then suitable for freeze drying with material to be encapsulated whereby the multilamella DRVs of greater than 0.1 μm diameter form.

In a third aspect of the present invention there is provided a method for separation of liposomes of the invention from non-entrapped microorganisms, cells or water insoluble structures characterised in that it places a mixture of the two on a density gradient and centrifuges it, the fractions of the gradient are removed, those containing the separated liposomes collected, and the liposomes separated from these by conventional methods; the free materials usually being collected in the lower fractions and the liposomes in the upper fractions. Preferably the gradient is a 0.4M to 4M sucrose gradient or gradient including an equivalent density range or analogous sugar. Where separation from soluble materials is also required the liposomes are centrifuged at approximately 600×g in buffer, eg. PBS, whereby they are collected as a pellet.

A fourth aspect of the present invention is therefor provided in the form of liposomes of the invention free from non-entrapped form of the undissolved or insoluble particulates they contain. Such forms are of course advantageous determination of dosage given.

As stated in the introductory paragraphs above, it is sometimes advantageous to present more than one agent to a target area of a patient simultaneously, and the present invention provides such advantage wherein the liposomes of the invention, the method of preparing them and the method of separating them from non-entrapped materials all incorporate or cater for handling of water soluble agent. Thus the liposomes produced by the method of the second aspect of the invention may contain living or attenuated microorganisms, cells and/or water insoluble structures together with water soluble agents such as vaccines, antibodies, antigens or enzymes.

Thus this method of preparing the liposomes of the invention will, when soluble materials are also to be incorporated, include the soluble material with the insoluble material with the liposomes in the rehydration step, preferably in the freeze drying step, and the method for separating non-entrapped material from the liposomes will utilise both the density gradient and buffer centrifugation methods.

A further aspect of the present invention, by virtue of the aforesaid aspects unique advantages, provides novel liposomes characterised in that they contain whole live or attenuated microorganisms, plant or animal cells, or water insoluble non-living structures having organic solvent labile biochemical or immunological activity. The latter will include killed organisms that retain a desired activity that is labile to organic solvent treatment. The liposomes of the present invention can readily be identified in that their content can be released and demonstrated to have retained the ability to be cultured and/or to illicit biochemical or immunological responses. In addition to bacteria, protozoans, cells or viruses, the liposomes of the present invention may comprise inanimate structures such as cytokine, enzyme, antigen or antibody bearing support materials, such as latex beads or other polymeric support bodies.

In a preferred form of this aspect the liposomes, and thus the approximate size of their vesicles, are from 0.1 μm to 50 μm in diameter, preferably from 1 μm to 30 μm, and conveniently 1 μm to 14 μm, with a convenient mean diameter being 5.5 μm+2.2; but vesicle size required will necessarily be dictated by the amount or size of solution, microorganism, cell or water insoluble structure that is intended to be encapsulated. To this end the means by which the liposomes are initially formed is not important, and thus variation in vesicle size is potentially unlimited as a method is provided for incorporating the labile materials, particularly microorganisms or insoluble structures, into already formed liposomes without killing or inactivating them or destroying liposome integrity.

Use of the liposomes of the present invention allows targeting of the macrophages, phagocytes and/or antibody producing cells of the body specifically, by virtue of the fact that the preferred liposomes, as stabilised with cholesterol, PG or equivalent materials, do not substantially release their particulate content spontaneously. Thus the fate of the particulate material tends to be in processing by macrophages or phagocytes whereby the immune response and related effects, eg, of cytokines, are enhanced. Furthermore, the fact that the particulate is protected from circulating antibodies by the lipid, until such encounter with the macrophages or phagocytes, ensures maximal presentation to the immune system and antibody producing cells.

The liposomes and methods of the present invention will now be illustrated by reference to the following Figures, non-limiting Examples, and Comparative Example. Many other suitable liposomes and methods for their preparation falling within the scope of the invention being readily evident to those skilled in the art in the light of these.

Formation of Giant Unilamella Liposomes

In these examples the giant liposomes are preformed, have a mean diameter of 5.5±0.2 μm and are mixed with the particulate or soluble materials and subsequently subjected to controlled rehydration.

Generated liposomes were found to maintain their original mean diameter and diameter range and to contain up to 26.7% (mean value) of the added materials. Particulate-containing liposomes could be freeze-dried in the presence of trehalose with most (up to 87%) of the entrapped material recovered within the vesicles formed on reconstitution with saline.

The sources and grades of egg phosphatidylcholine (PC), distearoyl phosphatidylcholine (DSPC), cholesterol, immunopurified tetanus toxoid and trehalose have been described elsewhere (Davis and Gregoriadis, 1987, Immunology, 61, 229–234). Phosphatidyl glycerol (PG) and triolein (TO) were from Lipid Products (Nuthill, Surrey) and Sigma Chemical Company (London) respectively. Killed *Bacillus subtilis* (*B.subtilis*) and Bacille Calmette-Guerin (BCG) were gifts from Dr Bruce Jones (Public Health Laboratories Service, Porton Down, Salisbury, Wilts) and Dr J. L. Stanford (Dept of Medical Microbiology, UCL Medical School, London) respectively. Radiolabelling of tetanus toxoid, B.subtilis, and BCG with $^{125}$I was carried out as described previously (Kirby and Gregoriadis, 1984 as above). Labelling of *B.subtilis* with fluorescein isothiocyanate (FITC) (Sigma) was carried out by incubating the bacteria in 1 ml 0.1M sodium carbonate buffer (pH9.0) containing 1mg FITC for 24 h at 4° C/ (Mann and Fish,(1972) Meth. Enzymology, 26, 28–42). All other reagents were of analytical grade.

A BRIEF DESCRIPTION OF THE DRAWING

FIGS. 1A and B show % added radioactivity or lipid v gradient fractions for a sucrose gradient centrifugation of giant liposomes containing $^{125}$I labelled *B. subtilis*. Separation of liposome-entrapped from non-entrapped *B. subtilis* (A) and of empty liposomes from added free *B. substilis* (B) was carried out by sucrose gradient separation as described below. Patterns of $^{125}$I radioactivity (○) and lipid (●) shown are typical for PC or DSCP liposomes prepared by either of the techniques described in the Comparative Example and Example 1 below. Values are % of radioactivity or lipid used for fractionation.

Figure 2A:
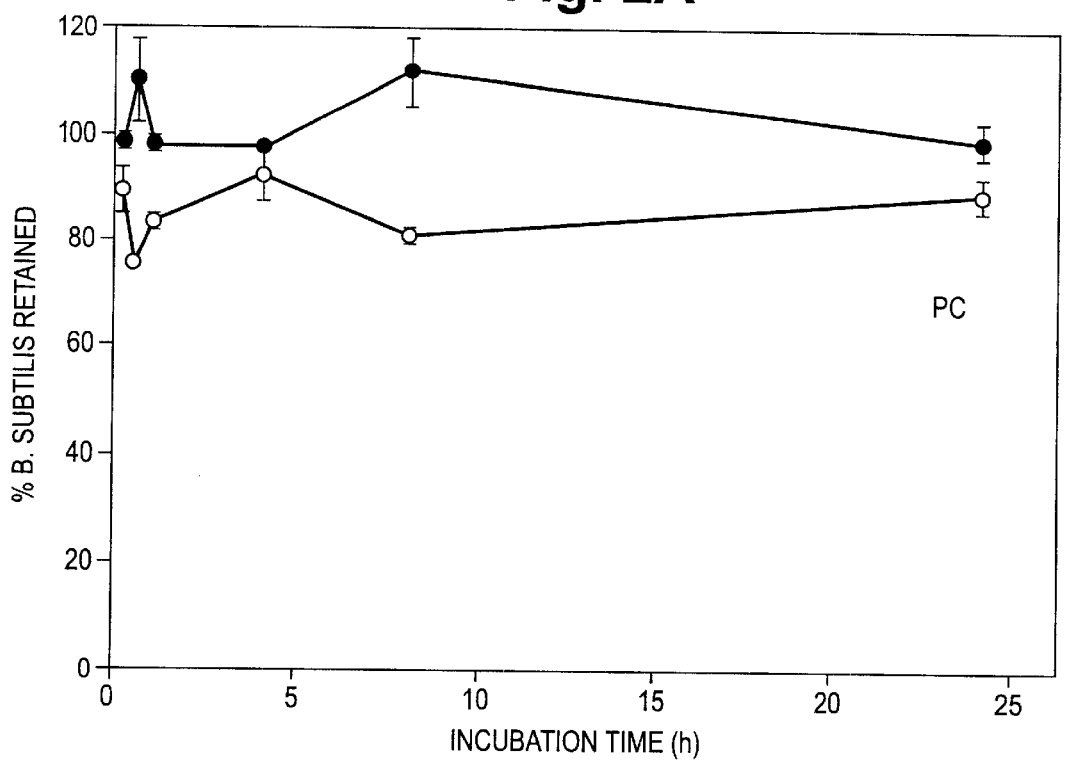
Figure 2B:
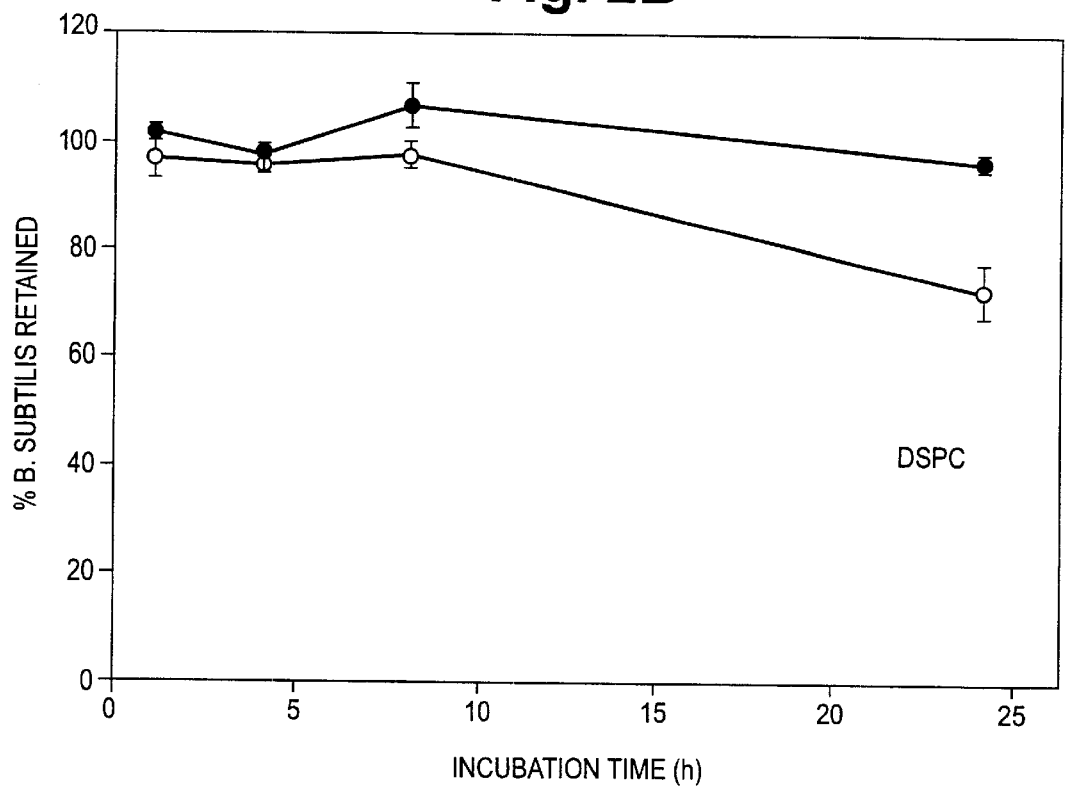

FIGS. 2A and B show % B. subtilis retention in liposomes of the invention v incubation time in plasma. PC or DSPC liposomes containing $^{125}$I labelled *B.subtilis* were incubated with mouse plasma (○) or PBS (●) at 37° C. At time intervals samples were fractionated on a sucrose gradient to separate freed from entrapped *B. subtilis* and values for triplicate experiments are %+SD of radioactivity recovered with liposomes.

Figure 3A:
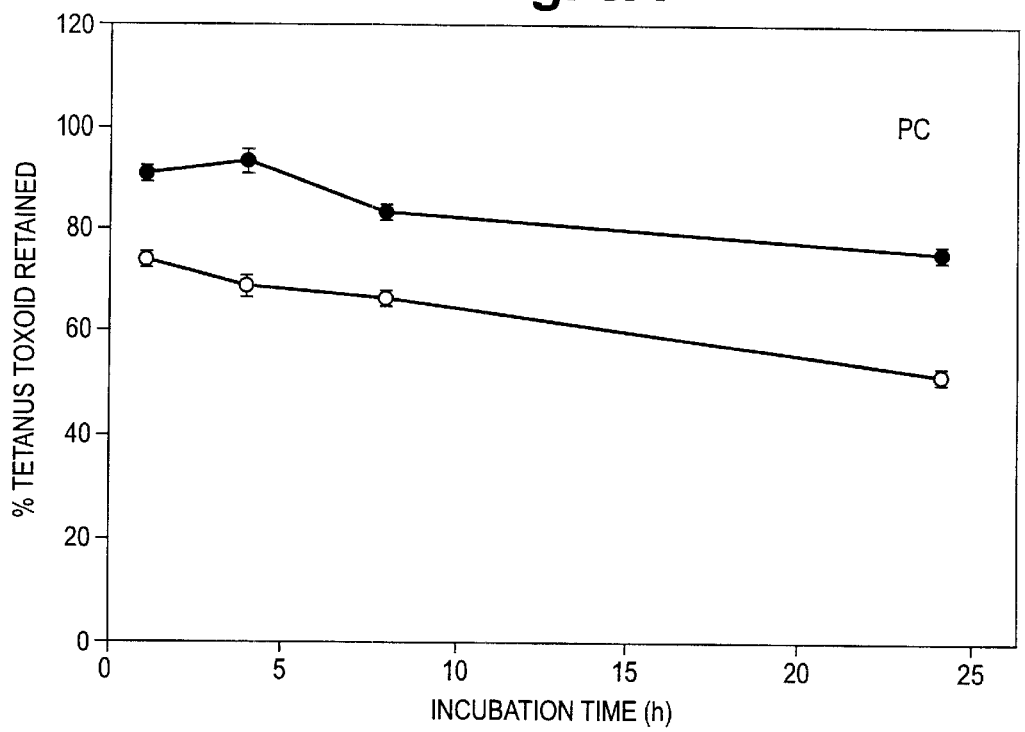
Figure 3B:
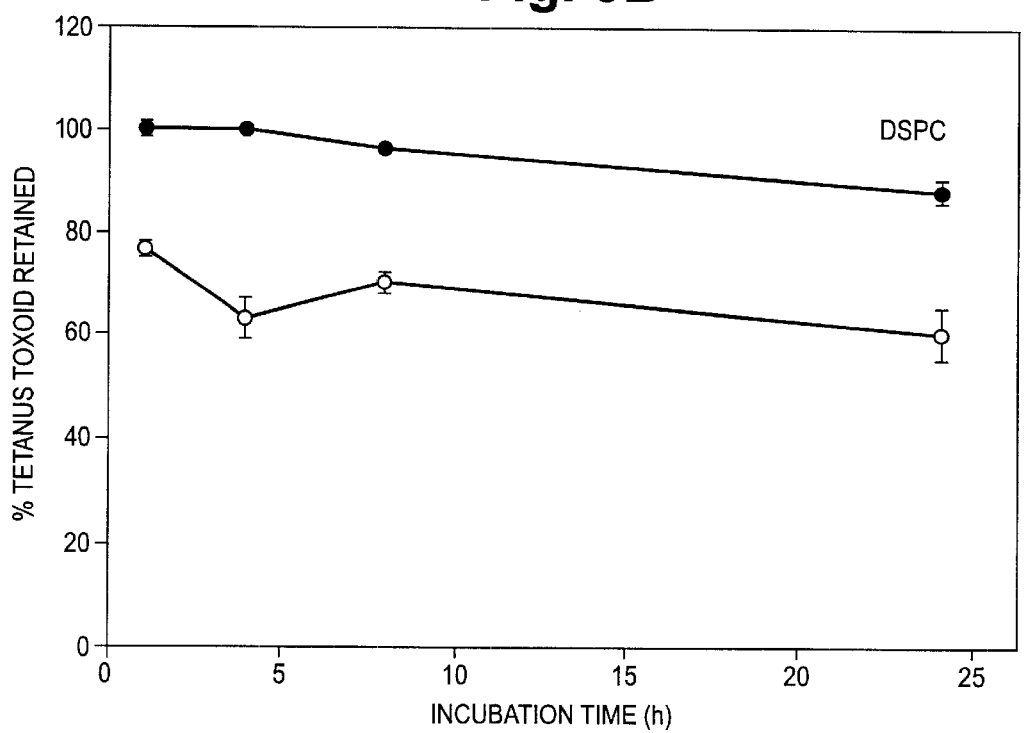

FIGS. 3A and B show retention of tetanus toxoid by liposomes of the invention in the presence of plasma. PC or DSPC liposmes containing $^{125}$I labelled tetanus toxoid were incubated in the presence of plasma (○) or PBS (●) at 37° C. At time intervals samples were centrifuged at 600×g to separate freed from entrapped toxoid. values from triplicate experiments are %+SD of radioactivity recovered with liposomes.

Figure 4A:
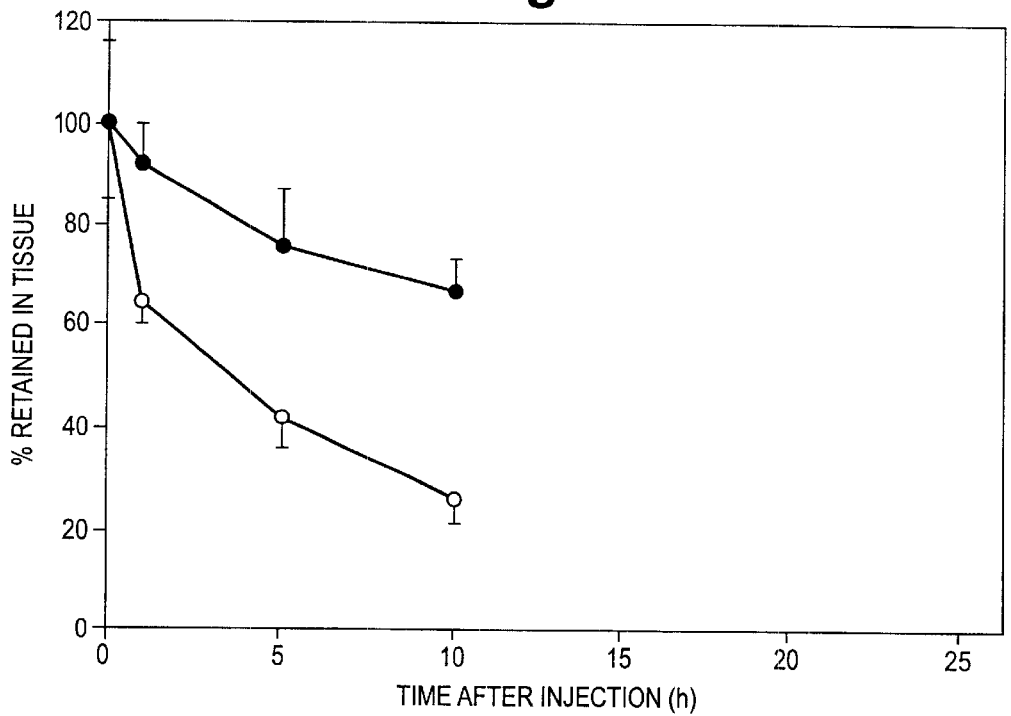
Figure 4B:
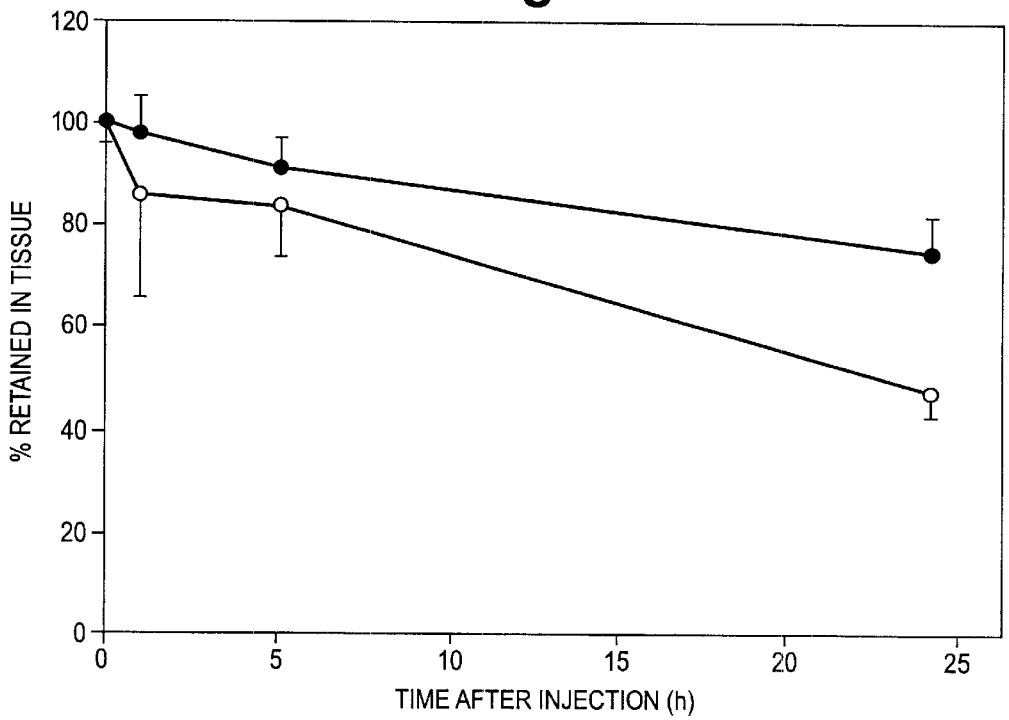

FIGS. 4A and B show clearance of tetanus toxoid and *B. subtilis* after intramuscular injection into mice. Mice were injected into their hind legs with free (○) or liposome entrapped (●) $^{125}$I labelled tetanus toxoid (A) or *B. subtilis* (B). Animals were killed at time intervals and radioactivity measured in the amputated leg. Each value represents three animals and is expressed as %+SD of the radioactivity recovered in the leg immediately after injection.

COMPARATIVE EXAMPLE

Preparation of Vaccine-Containing Giant Liposomes in the Presence of Organic Solvents.

Giant liposomes with entrapped materials were prepared by the solvent spherule evaporation method (Kim and Martin, 1981) with modifications.

In brief, 1 mL of a 0.15M sucrose solution containing the $^{125}$I-labelled material to be encapsulated (2×10$^3$–10$^4$ cpm; 1–2 mg tetanus toxoid and 10$^5$ *B.subtilis* bacteria as spores) was mixed by vortexing for 45 s with 1 mL of a chloroform solution containing PC or DSPC, Chol, PG and TO (4:4:2:1 molar ratio; 9 μmoles total lipid). The resulting water-in-chloroform emulsion was mixed by vortexing for 15 s with a diethyl ether-in-water emulsion prepared from 0.5 ml of a solution of the lipids as above in diethyl ether and 2.5 mL of a 0.2M sucrose solution. The water-in-oil-in-water emulsion thus formed was placed in a 250 mL conical flask and the organic solvents were evaporated by flushing nitrogen at 37° C. while the sample was gently agitated in a shaking incubator. Generated liposomes were centrifuged twice at 600×g for 5 min over a 5% glucose solution and the pellet was resuspended in 0.1 M sodium phosphate buffer supplemented with 0.9% NaCl, pH 7.4 (PBS). This last step enabled the separation of the entrapped from the non-entrapped toxoid. For the separation of non-entrapped *B.subtilis* (which sedimented together with liposomes) sucrose gradient fractionation was used (see below). In some experiments, FITC-labelled polystyrene particles (0.5 and 1 μm diameter; Polysciences) or FITC-labelled *B.subtilis* were entrapped as above in liposomes which were used in fluorescence microscopy studies.

Example 1

Entrapment of Live Vaccines in Preformed Giant Liposomes by Method of the Invention In order to entrap potentially labile particulate materials in giant liposomes in the absence of organic solvents, "empty" giant liposomes containing only sucrose were preformed as described in the Comparative Example above (with two preparations the total amount of lipid was 36 μmoles) and centrifuged over a 5% glucose solution in a bench centrifuge at 600×g for 5 min. The liposomal pellet was resuspended in 1 ml 0.1 M sodium phosphate buffer supplemented with 0.9% NaCl, pH 7.4 (PBS), mixed with 1 mL of a solution or suspension of the materials to be encapsulated (*B.subtilis* as spores, tetanus toxoid and BCG as spores) and freeze-dried as described previously (Gregoriadis et al, 1987; Kirby and Gregoriadis, 1984) by treatment under vacuum. Typically 2 ml of liposome suspension in distiled water were mixed with 2 ml of suspension or solution of material to be entrapped in a 50 ml round bottomed flask or 21 mm diameter glass tube, and the mixture flash frozen as a thin shell by swirling in a freezing mixture of cardice and isopropanol. After freezing the preparations were lyophilised, eg, in a Hetosicc freeze drier, at a vacuum of 0.1 torr for 4 to 5 hours, or 13Pa overnight.

The freeze-dried material was rehydrated initially by the addition of 0.1 mL distilled water at 20° C. (rehydration of liposomes containing the "high melting" DSPC at 50–600° C. did not have a significant effect on percent entrapment of materials). The suspension was vigourously swirled and allowed to stand for 30 min. The process was repeated after the successive addition of 0.1 mL PBS and of 0.8 mL PBS 30 min later. All materials for entrapment were $^{125}$I-labelled for assessing uptake. In one experiment, *B.subtilis*-containing liposomes prepared as above, were freeze-dried in the presence of 0.25M (final concentration) trehalose and subsequently reconstituted in PBS.

Example 2

Separation of Liposomes Containing Entrapped Material from Non-entrapped Material Separation of entrapped from non-entrapped material was carried out by sucrose gradient centrifugation (*B.Subtilis* and BCG; see below) or centrifugation at 600×g for 10 min followed by the suspension of the twice PBS-washed pellet in 1 mL PBS (tetanus toxoid). *B.subtilis* retention by the re-formed vesicles was evaluated by sucrose gradient fractionation. A discontinuous sucrose gradient was prepared (Gregoriadis, (1970) J. Biol Chem 245, 5833–5837) by layering ten dilutions (sucrose content ranging from 0.4M to 4M) of a 4M sucrose solution in swing out bucket centrifuge tubes. Preparations (1 mL) with entrapped and non-entrapped *B.subtilis* or BCG from Example 1 were placed on the top of the gradient and then centrifuged for 1.5 hours at 25,000rpm in a Dupont Combi Plus ultracentrifuge using a swing-out bucket. After centrifugation, 1 mL fractions were pippeted out from the top of the gradient and assayed for $^{125}$I radioactivity in a Wallac Minigamma counter and phospholipid content. (Stewart, (1979) Anal. Biochem, 104, 10–14). Separation of liposomes form sucrose fractions was carried out by diluting these with water or PBS, eg. using enough diluent to make up the volume to that of the centrifugation bucket, then centrifuging that at 600×g for 10 minutes as for removal of non-entrapped tetanus toxoid.

Measurement of vesicle size The mean diameter in terms of volume distribution of giant liposomes was measured in a Malvern Mastersizer.

Light Microscopy Light microscopy studies on liposomes containing FITC-labelled *B.subtilis* or polystyrene particles were carried out using a Nikon microscope and a Leica confocal microscope, both equipped with fluoresence light sources. To improve visualization of liposomes, these were stained by the addition of oil-red-0 in the chloroform solution of lipids during liposome preparation.

Stability of giant liposomes in plasma PC or DSPC giant liposomes (3–5 mg total lipid) containing radiolabelled toxoid ($10^3$ cpm; 0.1–0.2 mg) or B.subtilis (3–5×$10^3$ cpm; $10^3$ bacteria) and made by the method of the invention as in Example 1 and 2 were mixed in triplicates with five volumes of mouse (male, CDI strain) plasma or PBS and incubated at 37° C. At time intervals, samples were removed and retention of entrapped materials by liposomes was ascertained by sucrose gradient fractionation (B.subtilis) or centrifugation at 600×g (toxoid). Vesicle stability was expressed as percent of originally entrapped material retained by the vesicles.

Clearance of liposome-entrapped toxoid and B.subtilis after intramuscular injection into mice. Forty eight male CDI mice.(body weight 20–25 g) were randomly divided into four groups of twelve animals each and injected intramuscularly (hind leg) with 0.1 ml of (a) free radiolabelled toxoid (6×$10^3$cpm; 0.01 mg), (b) free radiolabelled B.subtilis (3X1O3cpm; $10^3$ bacteria as spores); (c) toxoid as in (a) entrapped by the method of Example 1 into DSPC liposomes (1 mg total lipid); (d) B.subtilis as in (b) entrapped into DSPC liposomes as in (c). Animals in groups of three, were killed and hind legs removed immediately after injection (to establish zero time values) and at time intervals thereafter. $^{125}$I was measured in the isolated legs and results were expected as percent of radioactivity recovered in the tissue at zero time.

RESULTS: EntraDment studies Evaluation of B.subtilis entrapment into giant liposomes could not be achieved by centrifugation as both entities sedimented at low speed. Complete separation was however, obtained by sucrose gradient fractionation as already described. The $^{125}$I radioactivity (B.subtilis) and phospholipid (liposomes) values measured in the fractions after centrifugation indicate that bacteria-containing PC or DSPC liposomes were recovered in the upper ten 0.5 ml fractions of the gradient, with free B.subtilis sedimenting to the bottom fraction.

The mean (+SD) diameter of these vesicles in eight different PC and DSPC preparations made according to the protocol of the examples was found to vary significantly (5.5±2.2 µm) with a lower and upper diameter range (all preparations) of 1–14 µm. There was no statistically significant difference in mean diameter between PC and DSPC liposomes. The possibility that bacteria had adsorbed to the surface of empty vesicles was discounted since incubation of such liposomes with B.subtilis for 22 hours prior to gradient fractionation resulted in the quantitative recovery of the latter in the bottom fraction. On the basis of B.subtilis presence in the top ten fractions of the sucrose gradient (which coincided with the presence of liposomal phospholipid in the same fractions), B.subtilis entrapment in twelve separate experiments by the method of Kim and Martin was variable with a mean value of 31.6% of the bacteria used. However, attempts to entrap tetanus toxoid by the same method (in the presence of organic solvents) failed presumably because of protein denaturation at the water-chloroform interface and subsequent inability of the altered protein to remain in the water phase.

This finding and the prospect of similar damage or otherwise inactivation of other protein antigens and attenuated or live microbes destined for entrapment demonstrates the advance of the method and product liposomes of the invention. Controlled rehydration of the powder obtained by freeze drying the preformed liposomes with B.subtilis, BCG and tetanus toxoid resulted in the formation of vesicles with a mean diameter (4.6±1.3 µm and a lower and upper range of 1–18 µm; all preparations) similar to those of the parent vesicles (see above), containing variable but substantial proportions of B.subtilis, BCG and toxoid (8.4 to 27.8% of the material used). There was no significant difference in values of B.subtilis entrapment obtained with the present procedure and that of Kim and Martin, but unlike in that method, ability to produce bacterial growth when liposome content was inoculated onto culture plates was retained.

Morphological Studies Light microscopy revealed that nearly all giant vesicles stained with oil red-O contained a varying number of FITC-labelled B.subtilis bacteria, which in many instances appeared to adhere to (or precipitate towards) the inner wall of the vesicles. Experiments using polystyrene particles and latex particles (0.5 µm and 1 µm in diameter) as particulate material for entrapment in 18 µm diameter liposomes gave similar results. That localization of particles within liposomes had been achieved was further evidenced by confocal microscopy which enabled their visualization in different "sections" of space within the vesicles.

Stability of giant liposomes in plasma An important prerequisite for the successful use of liposomes as carriers of live or attenuated microbial vaccines (alone or in combination with soluble antigens) in pre-immunized animals, animals with maternal antibodies to the vaccines, or with antibodies to vaccine impurities, would be avoidance of interaction between antibodies and vaccines prior to their delivery to antigen presenting cells. Previous work (Gregoriadis and Allison, 1974) demonstrated that such interaction was indeed avoided when protein containing multilamellar liposomes were injected intravenously into mice pre-immunized with the protein: whereas all animals injected with the free protein died of anaphylactic shock, those treated with the entrapped protein survived, presumably because of antigen confinement within the bilayers. Similarly, there was no Arthus reaction in such mice injected subcutaneously (foot pad) with the liposomal antigen (Gregoriadis and Allison, 1974). It was, therefore, of interest to see whether giant liposomes prepared by dehydration-rehydration would still retain their bacteria or tetanus toxoid content entrapped in the presence of mouse blood plasma at 37° C.

In the event B.subtilis-containing PC giant liposomes retained 80–90% of their bacteria content for at least 24 hours in the presence of plasma. As about 10% of bacteria were freed soon after mixing with plasma it is possible that these represent bacteria adsorbed to the liposome surface during entrapment and subsequently removed by plasma components. This is supported by the fact that liposomes exposed to PBS retained all their content B.subtilis. Retention of B.subtilis by DSPC liposomes in the presence of plasma was even greater (>95%) for at least 7 hours. Further, retention values were not significantly different than those seen in the presence of PBS, probably because a liposomal bilayer containing DSPC in its structure would be more rigid and therefore more resistant to particle adsorption. In contrast to the nearly quantitative retention of B.subtilis (dia 0.8 µm), giant liposomes appeared to gradually lose significant amounts or their toxoid content in the presence of plasma with the loss being more pronounced for PC (48%) than for DSPC liposomes (38%; 24 hour values).

Stability of giant liposomes in vivo after intramuscular injection The extent of tetanus toxoid and B.subtilis retention by giant liposomes after intramuscular injection into mice could not be estimated directly, for instance by measuring released and liposome-entrapped materials in the muscle tissue. However, it was reasoned that comparison of the clearance rates of free and liposome-entrapped tetanus toxoid and *B.subtilis* from the tissue could provide an indication of the extent to which liposomes retained their content in situ. Much more (67% of the content measured in the tissue immediately after injection) of the tetanus toxoid administered via liposomes was recovered in the tissue 10 hours after injection than toxoid given as such (27%). This substantial difference in clearance rates between the two toxoid formulations (entrapped and free) suggests that much of the liposomal toxoid is retained within the vesicles in situ.

It appears from the slow rate of liposomal toxoid clearance that liposomes are gradually destabilized to release toxoid which would then be cleared from the tissue as free. It is possible however that some of the vesicles, especially those of smaller size, may also migrate to the lymphatics. The rates of clearance of free and liposomal *B.subtilis* on the other hand, were initially similar. and assuming that liposomes containing *B.subtilis* or toxoid are destabilized (and release their contents) to the same extent in the local milieu, the slower clearance of liposomal *B.subtilis* (as compared to that of liposomal toxoid) during the first 5 hour is probably due to the similarly slow clearance of free bacteria. Nevertheless, the substantial difference in tissue levels between the two *B.subtilis* formulations 24 hours after injection indicates the considerable extent to which liposomes remain stable in the injected tissue.

Thus use of solvents detrimental to live or attenuated microbes and the presence of detergent in formulations rendering them toxic for in-vivo use has been demonstrated to be avoidable by use of the present invention. Liposomes prepared by the present procedure retain (in isolation from the external milieu) most of their bacteria or soluble antigen content in the presence of blood plasma and a considerable proportion of it in vivo. Thus, liposomes could not only serve as immunoadjuvants for microbial vaccines, in connection with co-entrapped soluble antigens or cytokines if required, but also as carriers of live or attenuated microbial vaccines in cases where there is a need to prevent interaction of the latter with maternal antibodies or preformed antibodies to vaccine impurities.

Furthermore, the present invention allows for the entrapment of microorganisms or cells within liposomes, followed by culturing of these in the entrapped state to increase the 'dose' of active material without the necessity to optimize the entrapment step. For example, only a few cells need be entrapped in the rehydration step, then these could be supplied with nutrients through the liposome wall, preferably with an inhibitor of lipid metabolism, such that they multiply thus making the liposome vesicle more heavily loaded with desired material. Once a suitable loading had been achieved, the liposomes would be freeze dried for storage, with rehydration being used just prior to use.
Formation of Multilamella Liposomes of the Invention Example 3

Entrapment of Live Spores and Other Materials in Multilamella DRV Liposomes

Small unilamella vesicles composed of PC or DSPC and equimolar cholesterol (18 $\mu$moles phospholipid) were prepared as described in Kirby and Gregoriadis, 1984) whereby phospholipid and cholesterol were dissolved in chloroform which was then rotary evaporated to leave a thin lipid film on the walls of the flask. The film was disrupted at 4° C. (PC) or 60° C. (DSPC) with 2 ml of distilled water and subsequently probe-sonicated for about 2 minutes to produce SUVs in suspension. The suspension was mixed with 2 ml of $^{125}$I-labelled live spores ($10^7$), 100–150 $\mu$g $^{125}$I-labelled toxoid or a mixture of radiolabelled spores and unlabelled toxoid and freez-dried overnight. The freeze-dried material was mixed vigorously with 0.1 ml water at the appropriate temperatures (as Example 2) and allowed to stand for 30 minutes. This step was repeated with 0.1 ml PBS and after 30 minutes the suspension supplemented with 0.8 ml PBS. The final suspension was subjected to sucrose gradient fractionation to separate the entrapped from non-entrapped spores or to centrifugation at 90,000×g twice for 20 minutes to separate the free from entrapped toxoid. Unlabelled toxoid was measured by the fluorescamine method (Anderson and Desnick (1979) J. Biol. Chem., 254, 6924)

Results: Spore entrapment was unexpectedly high (63.6–78%) inspite of previous findings of relatively small vesicle size for these type of vesicles. The mean size for PC-DRVs was 3.6 $\mu$m and for DSPC-DRVs was 3.2 $\mu$m diameter.
Spore Viability Giant or DRV liposomes containing *B.subtilis* spores were tested for spore viability by treating them with Triton X-100 to liberate spores were serially diluted in nutrient broth and then spread on nutrient agar plates to estimate the total colony count, the viability count and the average number of viable spores per individual vesicle. Results are shown in Table 1 below wherein the number of colonies are given.

The number of colonies produced for each treated preparation tested was much greater than that observed with intact liposomes; spores within an intact liposome being liable to only form a single colony. The table indicates that up to 20 spores could be found within individual vesicles with no apparent relationship between spore numbers and the phospholipid used. There was a positive relationship between the number of spores entrapped and vesicle size.

Among the six different giant liposome preparations used the lowest spore number was obtained with the smallest diameter of vesicle and the highest with the largest diameter vesicle. However, with DRV liposomes their smaller size was not reflected in lower spore numbers.

TABLE 1

Estimated average number of viable *B. subtilis* spores per vesicle.

| Type Method | Number of colonies | | Spores per vesicle | Vesicle size $\mu$m |
|---|---|---|---|---|
| | Triton | Control | | |
| Giant PC A | 96 | 29 | 3 | 6.3 |
| Giant DSPC A | 162 | 38 | 4 | 6.5 |
| Giant PC B | 203 | 10 | 20 | 8.4 |
| Giant DSPC B | 250 | 21 | 12 | 7.2 |
| Giant PC B | 160 | 12 | 13 | 8.0 |
| Giant DSPC B | 109 | 15 | 7 | 6.4 |
| DRV PC | 320 | 44 | 7 | 3.6 |
| DRV DSPC | 189 | 31 | 6 | 3.2 |

*B. subtilis* spores were entrapped in giant liposomes by method of the Comparative example (A), Example 1 (B), or DRV liposomes; both PC and DSPC lipids being used to make respective types. Estimation of spores per vesicle is carried out by dividing colonies number after triton treatment with the control number; the Triton number being equal to the number of viable spores liberated from vesicles. The control number is equivalent to the number of vesicles as entrapped spores produce only one colony. The toxic effect of the solvent (method A) on spores is demonstrated; this effect is increased on vegetative bacteria.

What is claimed is:

1. A method for forming unilamellar liposomes having a diameter of 0.1–20 μm containing one or more virus, protozoa or mixture thereof entrapped within the liposome, which method comprises the steps of:

(a) forming unilamellar liposomes of size sufficiently large to accommodate the virus and/or protozoa to be included therein, (b) freeze-drying the liposomes so formed in the presence of the virus and/or protozoa to be contained therein, and (c) hydrating the mixture from step (b) so as to form unilamellar liposomes containing the virus and/or protozoa.

2. A method for forming multilamella liposomes having a diameter of 0.1–20 μm containing one or more virus, protozoa or mixture thereof within the liposome, which method comprises the steps of:

(a) forming unilamellar liposomes of diameter less than that of the multilamellar liposomes to be produced, (b) freeze-drying the liposomes so formed in the presence of the virus and/or protozoa to be contained therein, and (c) hydrating the mixture from step (b) so as to form multilamellar liposomes containing the virus and/or protozoa.

3. A method as claimed in either of claims 1 or 2 wherein all of any organic solvents used in the preparation of the liposomes in step (a) is removed prior to step of freeze drying (b).

4. A method as claimed in either of claims 1 or 2 wherein prior to step (b) the virus and/or protozoa are intimately mixed with the liposomes.

5. A method as claimed in either of claims 1 or 2 wherein trehalose is added to the liposome product after rehydration as a protectant against the effects of water loss.

6. A method as claimed in either of claim 1 or 2 wherein step (c) is carried out by controlled addition of water in a quantity sufficient to produce a suspension, followed by a similar amount of phosphate buffered saline of about pH 7.4 and the suspension so obtained mixed with a larger volume of said phosphate buffered saline.

7. A method as claimed in either of claims 1 or 2 wherein the freeze drying step (b) is carried out by freeze drying a suspension of liposomes and virus and/or protozoa to be encapsulated and in rehydration step (c) water and saline are added in a total amount of from 1 to 10 times that of the volume of the suspension.

8. A method as claimed in either of claims 1 or 2 wherein the liposomes formed in step (a) comprise a lipid composition comprising phosphatidylcholine (PC) or distearoylphosphatidyl choline (DSPC) and wherein the lipid composition further comprises a member selected from the group consisting of cholesterol, phosphatidyl glycerol (PG), triolein (TO) and mixtures thereof.

9. A method as claimed in either of claims 1 or 2 wherein after the rehydration step (c) virus and/or protozoa are provided with nutrients through the liposome wall such that the virus and/or protozoa are cultured and multiply.

10. A freeze-dried intimate admixture of unilamellar liposomes and protozoa, which when rehydrated can form unilamellar liposomes, having a diameter of 0.1–20 μm, containing the protozoa.

11. A composition comprising a physiologically acceptable carrier and one or more liposomes as claimed in claim 10.

* * * * *